United States Patent [19]

Kakegawa

[11] 4,432,363

[45] Feb. 21, 1984

[54] APPARATUS FOR TRANSMITTING ENERGY TO A DEVICE IMPLANTED IN A LIVING BODY

[75] Inventor: Makoto Kakegawa, Ootawara, Japan

[73] Assignee: Tokyo Shibaura Denki Kabushiki Kaisha, Ootawara, Japan

[21] Appl. No.: 222,536

[22] Filed: Jan. 5, 1981

[30] Foreign Application Priority Data

Jan. 31, 1980 [JP] Japan .................................... 55-9307

[51] Int. Cl.³ ............................................. A61N 1/36
[52] U.S. Cl. ............................................. 128/419 PS
[58] Field of Search ........ 128/419 R, 419 PS, 419 PT, 128/1 R, 664, 773

[56] References Cited

U.S. PATENT DOCUMENTS

| | | | |
|---|---|---|---|
| 3,195,540 | 7/1965 | Waller | 128/419 PT |
| 3,209,081 | 9/1965 | Ducote et al. | 128/419 R |
| 4,143,661 | 3/1979 | Laforge et al. | 128/419 R |
| 4,202,339 | 5/1980 | Wirtzfeld | 128/419 PG |

FOREIGN PATENT DOCUMENTS 2212289 9/1972 Fed. Rep. of Germany ...... 128/419 PS

*Primary Examiner*—William E. Kamm
*Attorney, Agent, or Firm*—Finnegan, Henderson, Farabow, Garrett & Dunner

[57] ABSTRACT

Apparatus for applying energy to the outside of the skin for penetrating the skin, a transducer for converting the energy penetrating the skin to a form of energy utilizable by a device implanted in the body, and a member for transmitting the skin penetrating energy to the transducer. Preferably the applied energy is infrared light or heat with the transmitting member being optical fibers or a heat pipe, respectively, and the implanted device is a pacemaker for the heart, the battery of the pacemaker being rechargeable by the converted energy and the pulse generator of the pacemaker being controllable by the converted energy.

1 Claim, 4 Drawing Figures

APPARATUS FOR TRANSMITTING ENERGY TO A DEVICE IMPLANTED IN A LIVING BODY

BACKGROUND OF THE INVENTION

1. Field of the Invention

This invention relates generally to an energy-transmitting apparatus, and, in particular, to an apparatus which can easily supply energy to an apparatus implanted in a living body, such as a human body.

2. Description of the Prior Art

As to apparatus implanted in the body, a cardiac pacemaker is typically known which uses a mercury battery or a lithium battery as an energy source. However, the lifetime of almost all of these batteries is less than two years, so that, previously, the battery had to be periodically exchanged in anticipation of the termination of the battery life. On all such occasions, a physician had to perform a surgical operation for replacement of the battery and the patient is forced to undergo pain and expense which would otherwise be unnecessary. Also, if the pacemaker itself has some trouble, it may abnormally consume power, so that the battery life would be caused to be unexpectedly shortened. Although, in such an emergency, the battery should be immediately exchanged, this may not be possible. As a result, the life, dependent on the pacemaker, is threatened because of the need for the surgical operation and battery exchange. These possibilities bring a feeling of mental uneasiness to the patient and also the possible aggravation of the disorder requiring the pacemaker.

An atomic battery having a long life is known, which battery utilizes a radioisotope (RI) as a power source. Such apparatus, however, requires a radiation shield made of lead to protect the body from the x-rays emitted from the RI. The atomic battery is, therefore, not used conventionally because of its great weight and high price.

It has been recognized that the above-mentioned problems could be solved by the use of an implanted chargeable battery that could be recharged from outside the body. However, such a solution has been heretofore unrealizable because there has been no energy-transmitting apparatus which can interconnect a source of energy outside the body to the battery implanted in the living body without injuring the body.

SUMMARY OF THE INVENTION

It is accordingly one object of this invention to provide a simple, compact energy-transmitting apparatus, wherein the energy-transmitting apparatus can easily transmit energy to an apparatus previously implanted in the living body without performing an additional surgical operation.

It is another object of this invention to provide a simple, compact energy-transmitting apparatus, wherein the energy-transmitting apparatus painlessly transmits energy to apparatus previously implanted in a living body.

It is yet another object of this invention to provide an energy-transmitting apparatus, wherein the energy-transmitting apparatus can easily transmit energy to apparatus previously implanted in the living body at any time as required.

It is a more specific object of this invention to provide apparatus for easily recharging a battery previously implanted in a living body without further surgical procedures.

DESCRIPTION OF THE PREFERRED EMBODIMENT

Figure 1:
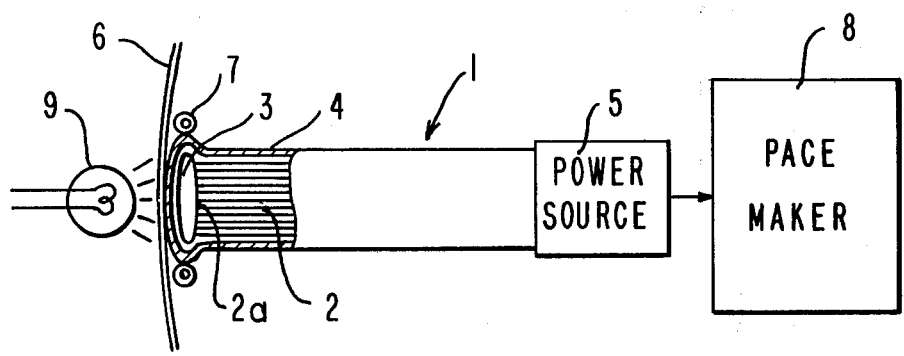
FIG. 1 is a partly sectional fragmentary schematic illustration showing an energy-transmitting apparatus according to a first embodiment of this invention.

Referring now to FIG. 1, there is shown a first embodiment of the invention, particularly one in which a light-transmitting apparatus supplies light energy in the form of infrared radiation to penetrate the skin of a living body, and then transforms the light energy to electrical energy for use by implanted apparatus, such as a pacemaker.

In FIG. 1 reference numeral 1 designates an energy-transmitting member which comprises a bundle of optical fibers 2, a condensing lens 3 as an input terminal and a protective membrane 4, formed of silicone rubber which covers the optical fibers and the condensing lens. The input terminal of the energy-transmitting member 1 is disposed adjacent the inner surface of the skin 6 of a living body, and preferably is stitched to the skin. Preferably the energy-transmitting member has a circular cross section, and an annular projection 7 is formed in the protective membrane 4 about the input terminal end for facilitating the attachment of the member to the skin as by sewing. The output end of energy-transmitting member 1 is connected to an electric power source 5 including, for example, a solar battery of a pacemaker 8 implanted adjacent the heart. Numeral 9 indicates a light source, such as an infrared lamp, for supplying energy through the skin and the energy-transmitting member to the power source 5 from outside of the living body. Moreover, if the light source 9 is of high performance, there is no necessity for using the condensing lens of the energy-transmitting member.

Figure 2:
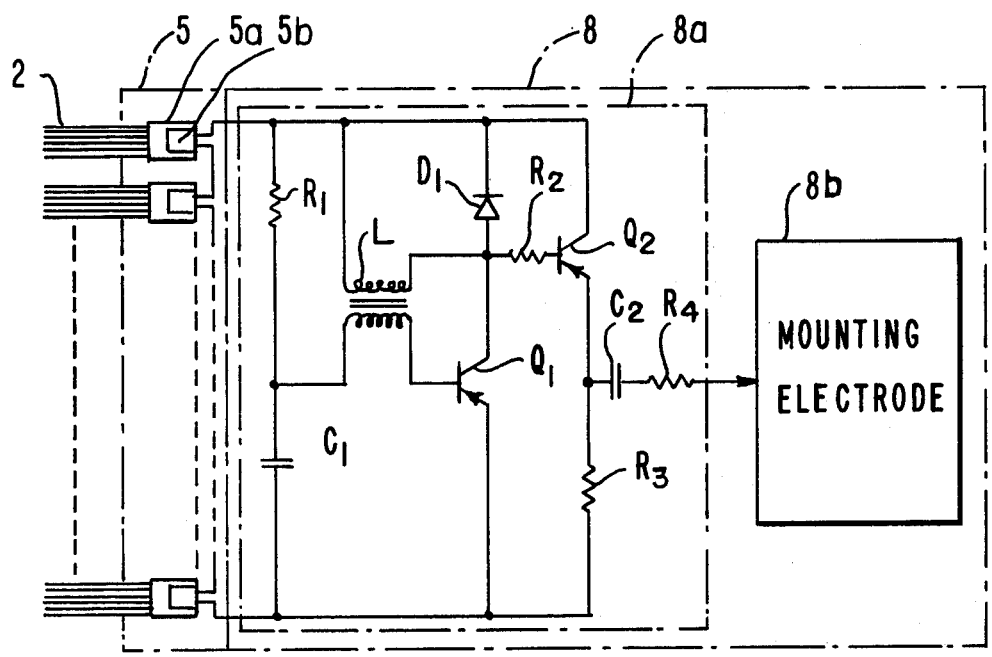
FIG. 2 is a circuit diagram showing one form of electric circuit for use with the invention.

Referring now to FIG. 2, there is shown one form of a detailed construction including the optical fibers 2, the power source 5 and the pacemaker 8. The power source 5 is composed of solar battery including a photoelectric converter 5a, such as a photodiode, which is coupled to the output ends of the optical fibers 2.

The pacemaker 8 comprises a conventional pulse generator 8a actuated by the solar battery 5 and a mounting electrode 8b for supplying rhythm to the heart. The pulse generator includes a resistor $R_1$ and a condenser $C_1$ connected across the battery for determining an oscillation time constant value, an oscillation coil L, a diode $D_1$ and a switching transistor $Q_1$ constructed as a so called blocking oscillator. $Q_2$ denotes an emitter follower transistor of which the gate is connected to a connection point of the diode $D_1$ and the switching transistor $Q_1$ through a biasing resistor $R_2$, the collector is connected to a positive terminal of the battery and the emitter is connected to a negative terminal of the battery through a biasing resistor $R_3$. An oscillation output acquired from the emitter of the transistor $Q_2$ is adapted to be supplied to the electrode 8 through a condenser $C_2$ and a resistor $R_4$.

Next, explaining about the operation of the pacemaker and the charging method of the battery, the pacemaker 8 operates in the manner that the pulse generator 8a is actuated by a voltage supply from the source 5 for causing an oscillation output which is supplied to the electrode 8b to supplement the rhythm of the heart. The oscillation output frequency is determined by the time constants of the resistor $R_1$ and condenser $C_1$. In due consideration of the lifetime of the source, i.e., the solar battery 5, the battery is periodically charged by bringing the infrared lamp in close proximity to the living body skin. As the skin and the silicone rubber membrane have an infrared transmission property, the infrared radiation from the infrared lamp 9 is condensed by the condenser lens 3 of the energy-transmitting member 1, is entered into the optical fibers 2 from their input ends 2a, and is led into the power source 5 through the outer ends of the optical fibers. The photoelectric converter 5a generates electromotive force to charge the battery 5b. If the above-described energy-transmitting member is used, the power source such as the battery of the pacemaker could be easily charged by supplying infrared radiation from outside the living body. Therefore, there is no necessity for performing a second surgical operation for the battery exchange as in the past. Furthermore, the feeling of mental uneasiness and the pain of the patient are excluded and the problem that threatens the life of the patient through failure of replacement of the battery is minimized.

The energy-transmitting member of the invention has several distinct advantages, such as (1) the silicone rubber protective membrane is non-tissue reactive and will not injure the human anatomy; (2) the optical fibers in the silicone rubber protective membrane can be bent and are, therefore, easy to position; (3) the energy-transmitting efficiency of the member is not affected by external electronic noise; and (4) a bundle of optical fibers is much lighter in weight than an electric cable and, therefore, more comfortably borne in the body.

Figure 3:
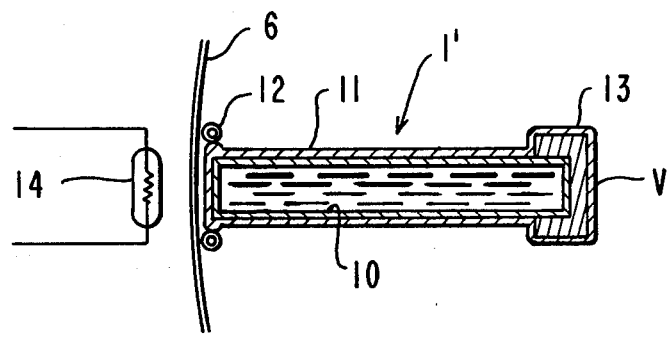
FIG. 3 is a schematic sectional view showing an energy-transmitting apparatus according to a second embodiment of the invention.

FIG. 3 shows another embodiment of the energy-transmitting apparatus according to the invention wherein a heat pipe is used as the energy-transmitting member. That is, this energy-transmitting member 1' comprises a pipe-shaped water-containing porous layer 10, a so-called "wig", and a protective membrane, such as a silicone rubber membrane 11. The input end of the heat pipe is disposed adjacent the inner surface of a living body skin and stitched and preferably thereto by means of a projection 12 defined on the protection membrane 11. The output end of the heat pipe is coupled to a thermo-electric converter such as a thermocouple or a thermopile. The output terminal of the charge of the battery is carried out by disposing a heater 14 outside of the living body skin. When the heater 14 is heated to about 40° C., water in the wig 10 is evaporated by the heat and moved from the input end to the output end of the heat pipe, so that the output end is heated at about 40° C. Consequently, the thermocouple or thermopile coupled to the output end of the heat pipe generates electromotive force to charge the battery. Namely, the energy-transmitting member 1' has the function of transmitting heat energy from the heat source such as heater 14. The embodiment utilizing the heat pipe has the same advantages in transmitting energy as stated for the first embodiment.

Figure 4:
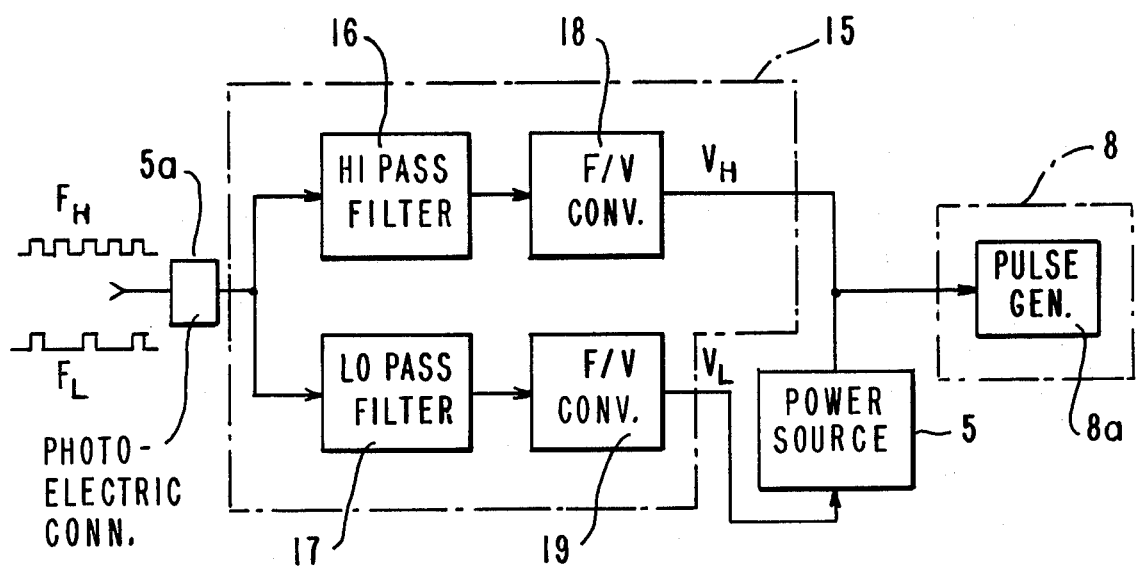
FIG. 4 is a block diagram depicting another application of an energy-transmitting apparatus according to the invention.

Although the above-mentioned embodiments both relate only to apparatus through which a battery is charged, the energy-transmitting apparatus according to the invention can also control the action of the apparatus implanted in the living body. For example, this result can be accomplished by putting control apparatus 15 such as shown in FIG. 4, at the front of the pacemaker 8. The control apparatus 15 comprises a high-pass filter 16, a low-pass filter 17, and F/V converters 18, 19 which, respectively, convert output frequency signals F of the high-pass filter 16 and the low-pass filter 17 to voltage signals $V_H$ and $V_L$. The output $V_H$ of the F/V converter 18 is supplied to the source terminal of the pacemaker 8, while the output $V_L$ of the F/V converter 19 is supplied to the charge terminal of the power source.

The above-mentioned apparatus is to be implanted in the living body wherein the output terminal of the energy-transmitting apparatus shown in FIG. 1 is to be connected to the photoelectric converter 5a. With this arrangement, either of two light pulse signals $F_H$, $F_L$ which respectively have different frequencies, can be externally applied. The low frequency pulse $F_L$ can be used, for example, for charging the battery of the source 5 and the high frequency pulse $F_H$ can be used for raising or lowering the oscillating output frequency of the pacemaker 8. For example, by the supply of the low-frequency pulse signal $F_L$, this frequency pulse passes only through the low-pass filter 17 to be applied to the F/V converter 19 of which the output $V_L$ charges the battery. During the charging of the battery, the pacemaker 8 continues to generate the oscillating frequency signal supported by the battery voltage of the source 5. On the other hand, by the supply of the high-frequency pulse signals $F_H$, this frequency pulse passes only through the high-pass filter 16 to be applied to the source terminal of the pacemaker 8. Since the $V_H$ is higher than battery voltage $V_L$, the current which flows into the time constant resistor $R_1$ and condenser $C_1$ of the pulse generator 8a may be used to vary the oscillating frequency of the pacemaker.

Since the oscillating output of the pacemaker can be controlled as above-mentioned, for example, when the patient is in the state of rest the rhythm of the heart can be controlled in conformity with the normal frequency, and when the patient is in the state of motion (especially in the state of running) the rhythm of the heart can be quickly increased by raising the oscillating frequency of the pacemaker.

Moreover, the pacemaker may be constructed with a voltage-frequency (V/F) converter of which the input terminal is connected to a changeover switch, and a plurality of energy signals which are respectively different may supply different voltages to the V/F converter through the changeover switch for controlling the pacemaker at different rhythms.

Since the energy-transmitting apparatus according to the invention is provided with the construction aforementioned, it can be extensively applied for supplying energy to apparatus implanted in the living body without being limited to a pacemaker.

What I claim is:

1. Apparatus for supplying energy from a source outside a living body to a device having an energy supply terminal implanted in the body comprising:
   means having an input adjacent the inside surface of the skin of the living body and including a bundle of optical fibers for transmitting light energy from said input to an output, said input also including a condensing lens for transmitting said light energy to said bundle of optical fibers, a protective membrane covering said bundle of optical fibers and said condensing lens;

an annular projection formed in said protective membrane and surrounding said condensing lens for facilitating the attachment of the apparatus to the inside surface of the skin by sewing;

means for receiving said light energy from said output, for converting said light energy to electrical energy, and for applying said electrical energy directly to the energy supply terminal of said implanted device; and energy source means for applying light energy to the outside surface of the skin of the living body opposite said input of the energy-transmitting means, said applied light energy penetrating the skin without rupturing the skin and entering said input.

* * * * *